United States Patent [19]

Hamprecht

[11] Patent Number: 5,011,927
[45] Date of Patent: Apr. 30, 1991

[54] PREPARATION OF 2-AMINO-4-FLUOROPYRIMIDINE DERIVATIVES

[75] Inventor: Gerhard Hamprecht, Weinheim, Fed. Rep. of Germany

[73] Assignee: BASF Aktiengesellschaft, Ludwigshafen, Fed. Rep. of Germany

[21] Appl. No.: 452,106

[22] Filed: Dec. 18, 1989

[30] Foreign Application Priority Data

Jan. 10, 1989 [DE] Fed. Rep. of Germany ....... 3900471

[51] Int. Cl.$^5$ .......................................... C07D 239/47
[52] U.S. Cl. .................................... 544/320; 544/321
[58] Field of Search .............................. 544/320, 321

[56] References Cited

FOREIGN PATENT DOCUMENTS 0073627 3/1983 European Pat. Off. .

OTHER PUBLICATIONS

Chemical Abstracts (I), 85:77134, 1976.
Chemical Abstracts (II), 80:59913, 1974.
Chemical Abstracts (III), 80:14409, 1974.
J. Med. Chem. 6, 688 ff, 1963.
J. Chem. Soc. 6, 1280 ff, 1970.
SU-A 547 447 (1975), no equivalent abstract in CA 86, 190 000.
Schwamborn et al., Chem. Abst. 105-2232n (1986).
Ito et al. Chem. Abst. 107-134323u (1987).

Primary Examiner—Cecilia Shen
Attorney, Agent, or Firm—Keil & Weinkauf

[57] ABSTRACT

A process for the preparation of 2-amino-4-fluoropyrimidine derivatives of the general formula I

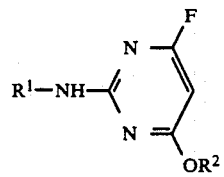

($R^1$ hydrogen, alkyl, alkenyl, alkynyl, cycloalkyl, phenyl or benzyl, it being possible for the aromatic rings to be substituted, and $R^2$ one of the $R^1$ radicals with the exception of hydrogen) by reaction of 2,4,6-trifluoropyrimidine in an aprotic polar organic solvent with an amine of the formula III to give the 2-aminodifluoropyrimidine derivative IVa mixed with the 4-aminodifluoropyrimidine derivative IVb, separation of IVa out of the resulting reaction mixture and subsequent reaction of IVa with an alcohol in the presence of a base at from 0° to 180° C. to give the 2-amino-4-fluoropyrimidine derivative I, by carrying out the reaction of 2,4,6,-trifluoropyrimidine II with the amine III at from −80° C. to −15° C., and reacting the 2-aminodifluoropyrimidine derivative IVa with the alcohol in the presence of an organic base to give the 2-amino-4-fluoropyrimidine derivative I.

12 Claims, No Drawings

PREPARATION OF 2-AMINO-4-FLUOROPYRIMIDINE DERIVATIVES

The present invention relates to an improved process for the preparation of 2-amino-4-fluoropyrimidine derivatives of the general formula I

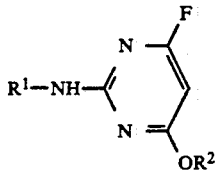

where $R^1$ is hydrogen, alkyl, alkenyl, alkynyl, cycloalkyl, phenyl or benzyl, it being possible for the aromatic rings to be substituted once to three times by radicals inert to the reaction conditions, $R^2$ is one of the $R^1$ radicals with the exception of hydrogen, by reaction of 2,4,6-trifluoropyrimidine (II)

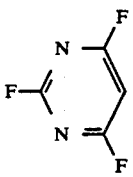

in an aprotic polar organic solvent with an amine of the formula III $$R^1\text{—NH}_2 \qquad \text{III}$$

to give the 2-aminodifluoropyrimidine derivative of the formula IVa mixed with IVb

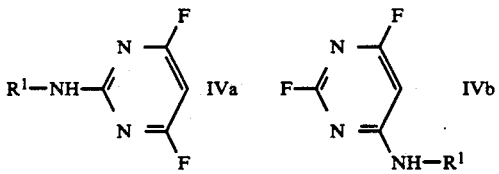

separation of IVa out of the resulting reaction mixture and subsequent reaction of IVa with an alcohol of the formula V $$R^2\text{—OH} \qquad \text{V}$$

in the presence of a base at from 0° to 180° C. to give the 2-amino-4-fluoropyrimidine derivative of the formula I, or by reaction of 2,4,6-trifluoropyrimidine II in an inert organic solvent in the presence of a base with an alcohol of the formula V to give the 2,4-difluoropyrimidine ether VIa mixed with the 4,6-difluoropyrimidine ether VIb

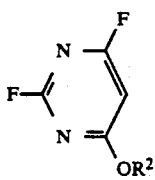

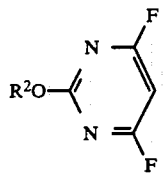

separation of VIa out of the resulting reaction mixture and subsequent reaction of VIa in an aprotic polar solvent with an amine of the formula III to give the 2-amino-4-fluoropyrimidine derivative I.

The literature (J.Med.Chem. 6 (1963) 688) discloses the reaction of 2,4,6-trifluoropyrimidine (II) with ammonia to give a mixture of 2-amino-4,6-difluoropyrimidine IVa' and 4-amino-2,6-difluoropyrimidine IVb', the isolation of IVa' and IVb', and the reaction of the isomer IVa' with methanol, ethanol and benzyl alcohol V' to give the 2-amino-4-fluoropyrimidine derivatives I'.

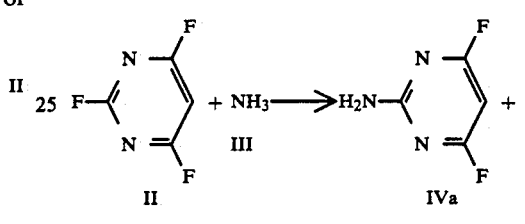

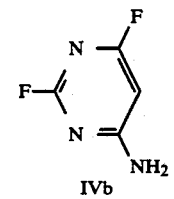

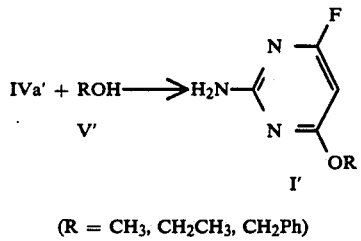

($R = CH_3, CH_2CH_3, CH_2Ph$)

This entailed, in the first stage of the synthesis, absolute ethanol being saturated with ammonia at 0° C., and a solution of 2,4,6-trifluoropyrimidine (II) and ethanol then being added to the solution obtained in this way. It was possible, after elaborate separation of the isomers, to isolate 2-amino-4,6-difluoropyrimidine IVa' in 54.9% yield.

The further reaction of the 2-aminodifluoropyrimidine midine IVa' obtained in this way with the alcohols V' was carried out with the corresponding sodium salts in the alcohol itself (for methanol and ethanol) or in toluene (for benzyl alcohol) at from 55° to 110° C. and provided the desired 2-amino-4-fluoropyrimidine derivative in a crude yield of 90% of theory ($R=CH_3$), 61% of theory ($R=CH_2CH_3$) and 64% of theory ($R=CH_2Ph$).

Two other methods for synthesizing 2-amino-4,6-difluoropyrimidine (IVa') have been described in the literature.

Banks et al. (J.Chem.Soc. C (1970) (9), 1280–5) reacted 2,4,6-trifluoropyrimidine (II) at 0° to 25° C. with a saturated solution of ammonia in tetrahydrofuran and obtained the mixture of the isomers IVa' and IVb' in the ratio of 67:33 in 79% yield.

SU-A 547,447 (1975) described this reaction in diethyl ether at from −10° C. to 25° C., resulting in the isomers IVa' and IVb' in the ratio 85:15 in 99% overall yield. The reaction of IVa' with sodium benzylate which is likewise described therein takes place under conditions similar to those already quoted (J.Med.-Chem.).

The essential problem with these syntheses of 2-amino-4-fluoropyrimidine derivatives I is the preparation of pure IVa. In addition, the reaction of IVa with the sodium alcoholate also provides only crude products from which the desired derivatives can be isolated only with losses of yield.

Hence the object of the present invention was to develop a more straightforward process which is also more economic for the industrial scale and which permits easier and more efficient working up.

In accordance with this object, we have now found a process for the preparation of the 2-amino-4-fluoropyrimidine derivatives of the formula I, which are defined in the introduction, by reaction of 2,4,6-trifluoropyrimidine (II) in an aprotic polar organic solvent with a solvent polarity $E_T^N$ below −0.35 with an amine of the formula III wherein the amine III is employed in 1.8 to 2.2 mol-equivalents relative to II.

$$R^1-NH_2 \qquad \qquad III$$

to give the 2-aminodifluoropyrimidine derivative IVa mixed with IVb

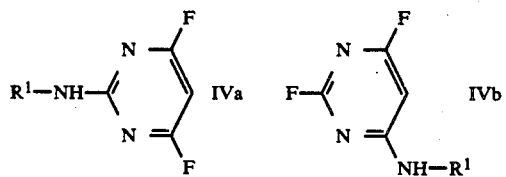

separation of IVa out of the resulting reaction mixture and subsequent reaction of IVa with an alcohol of the formula V $$R^2OH \qquad \qquad V$$

in the presence of a base at from 0° to 180° C., which comprises carrying out the reaction of the 2,4,6-trifluoropyrimidine at from −80° C. to −15° C., and reacting the 2-aminodifluoropyrimidine derivative IVa with the alcohol V in the presence of an organic base to give the 2-amino-4-fluoropyrimidine derivative I.

However, it is also possible to obtain the 2-amino-4-fluoropyrimidine derivatives I by first reacting 2,4,6-trifluoropyrimidine (II) with the alcohol V at from −40° C. to 120° C. and, after isolation, to react the difluoropyrimidine ether VIa obtained in this way with the amine III at from −40° C. to 100° C. to give the 2-amino-4-fluoropyrimidine derivative 1.

Both routes are depicted in the reaction scheme below:

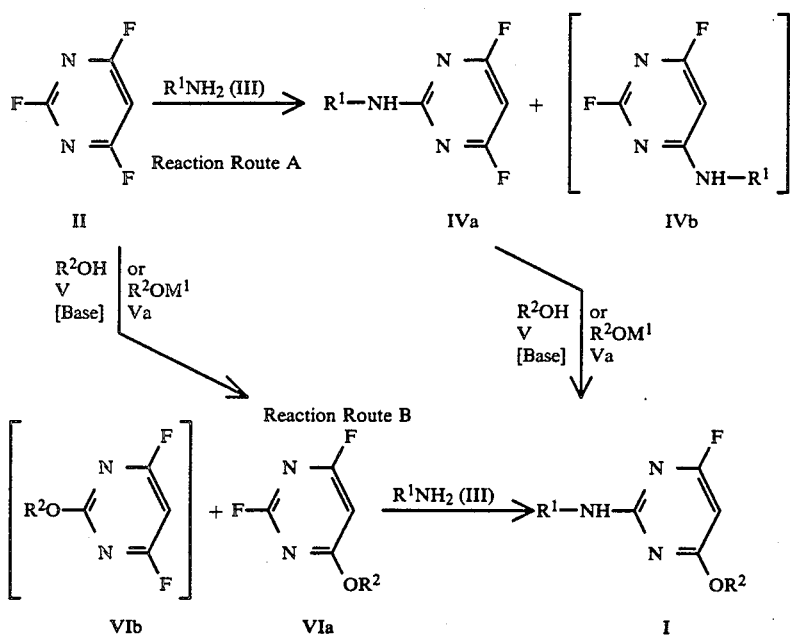

$M^1$ in formula Va is an alkali metal cation such as a lithium, sodium and potassium cation or the equivalent of an alkaline earth metal cation such as a magnesium, calcium and barium cation.

Thus, compounds I are prepared by two independent reaction routes (A and B). Reaction route A 2,4,6-Trifluoropyrimidine II can be reacted in an aprotic polar solvent with an amine III, which can be in aqueous solution, at from −80° to −15° C., after which the 2-aminopyrimidine derivative IVa, which has been obtained in this way and isolated, is reacted without solvent or in the presence of an inert organic solvent either with an alcohol V in the presence or absence of an organic base or with an alcoholate Va in the presence of the corresponding alcohol V or of a cation-complexing solvent at from 0° to 180° C. to give the 2-amino-4-fluoropyrimidine derivative I. These reactions can be carried out under atmospheric or superatmospheric pressure (1 to 10 bar, preferably 1 to 5 bar), continuously or discontinuously.

The following solvents are suitable for the reaction of 2,4,6-trifluoropyrimidine II with the amine $R^1NH_2$ III to give IVa and IVb: Ethers such as methyl tert.-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters such as ethyl acetate, n-butyl acetate and iso-butyl acetate as well as chlorinated hydrocarbons such as 1,1,2,2-tetrachloroethane, 1,1-dichloroethylene, chlorobenzene, 1,2-dichlorobenzene and 1-chloronaphthalene and mixtures of these solvents.

The solvent is expediently used in an amount of from 100 to 2000% by weight, preferably 500 to 1500% by weight, relative to the starting material II.

It is advantageous to add 1.85 to 2.15 mol-equivalent of the amine III, relative to the starting material II, within 1 to 2 hours to a mixture of starting material II in one of the above mentioned solvents at from $-80°$ to $-15°$ C., preferably $-30°$ to $-15°$ C., then to stir for up to one hour until the reaction is complete, and then allow to warm to 25° C. for working up.

The reaction of the intermediate IVa with the alcohol V is expediently carried out directly in excess alcohol V as the solvent. It may be advantageous to add an alcoholate Va to increase the reaction rate. In general, this alcoholate will be added to a suspension of the starting material IVa in 5 to 30 times the amount by weight of alcohol V as solvent, relative to the starting material IVa, within one hour at from 20° to 80° C. To complete the reaction, the mixture is then stirred at from 0° to 140° C., preferably 20° to 100° C., for 0.5 to 8 hours.

Examples of suitable alcoholates Va are lithium, sodium, potassium, calcium, barium and magnesium salts. However, also suitable in place of the alcoholates for increasing the reaction rate are organic bases such as trimethylamine, triethylamine, N-ethyldiisopropylamine, triisopropylamine, N,N-dimethylaniline, N,N-dimethylcyclohexylamine N-methylpyrrolidine, pyridine, quinoline, $\alpha$, $\beta$ or $\gamma$-picoline, 2,4- and 2,6-lutidine and triethylenediamine.

In a particular embodiment of the process according to the invention it is possible to react the 2-aminodifluoropyrimidine derivative IVa with an alcoholate Va in an organic solvent which complexes the cations.

Examples of complexing solvents of this type are dimethyl sulfoxide, dimethylformamide and N-methyl-2-pyrrolidone. These solvents are normally employed in 5 mol-equivalent to 15 mol-equivalent relative to IVa, and the alcoholate Va is employed in 0.9 mol-equivalent to 1.2 mol-equivalent relative to IVa.

This reaction can be carried out at, preferably, from 60° to 180° C., especially 80° to 150° C., continuously or discontinuously. Reaction route B Where 2,4,6-trifluoropyrimidine is etherified in the first reaction stage with an alcohol V, and the pyrimidine ether VIa formed in this way is subsequently converted with the amine III into the 2-amino-4-fluoropyrimidine derivative I, these reactions take place under conditions similar to those described above in the same solvents and using the same bases and the same ratios of amounts.

The reaction of 2,4,6-trifluoropyrimidine (II) with the alcohol V can also be carried out in the absence of a base.

The temperature for the reaction of II with the alcohol V or the salt Va thereof is from -40 to 120° C., preferably from $-20°$ to 100° C., and for the reaction of VIa with an amine III is from $-40°$ to 100° C., preferably from $-20°$ to $+40°$ C.

The reaction times for both reactions are up to 6 hours.

The working-up methods for isolating the aminopyrimidines I are those described for this purpose in the literature.

The advantage of reaction route A compared with the state of the art is that isomer-free 2-amino-4,6-difluoropyrimidine IVa is obtained rapidly and directly in a main reaction without additional washing and recrystallization processes and without steam distillation which entails large losses. Moreover, the following reaction with alcohols provides pure 6-alkoxy-2-amino-4-fluoropyrimidines I directly.

The advantage of reaction route B compared with the state of the art is that the alkoxypyrimidines VIa and VIb are obtained in higher overall yields [compared with J.Chem.Soc. C (1970) (9) 1280–5] and are easily separated by distillation [without a steam distillation entailing large losses, compare J. Med. Chem. 6 (1963) 688], as well as the possibility of base-free reaction (Example 15) and the isomer-free amination to give I.

$R^1$ in the starting materials III can be hydrogen, alkyl, alkenyl, alkynyl, cycloalkyl, phenyl or benzyl, it being possible for the aromatic rings to be substituted once to three times by radicals inert to the reaction conditions.

$R^1$ is particularly preferably hydrogen; alkyl such as methyl, ethyl, propyl, 1-methylethyl, n-butyl, 1-methylpropyl, 2-methylpropyl and 1,1-dimethylethyl as well as n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl and octyl, preferably methyl, ethyl, propyl, 1-methylethyl and 1,1-dimethylethyl; alkenyl such as allyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1,2-dimethyl-2-propenyl, 1,1-dimethyl-2-propenyl, 1-methyl-3-butenyl, 1-ethyl-2-propenyl, 2-hexenyl, 1-methyl-2-pentenyl, 1-ethyl-2-butenyl and 2-ethyl-2-butenyl, preferably allyl, 2-butenyl and 3-butenyl; alkynyl such as 2-propynyl, 2-butynyl, 3-butynyl, 1-methyl-2-propynyl, 1-methyl-2-butynyl, 1-ethyl-2-propynyl, 2-pentynyl, 3-pentynyl, 4-pentynyl and 1-methyl-2-pentynyl, preferably 2-propynyl; cycloalkyl such as cyclopropyl, cyclobutyl, cyclopentyl, cyclohexyl, cycloheptyl and cyclooctyl, preferably cyclopropyl, cyclobutyl, cyclopentyl, cyclohexyl and cycloheptyl.

$R^2$ in the starting materials V and Va can be, preferably, one of the radicals mentioned for $R^1$, but not hydrogen.

By comparison with the state of the art, the process according to the invention provides the compounds I in better yield and purity in all steps by a more straightforward and economic route.

The 2-amino-4-fluoropyrimidine derivatives of the formula I which can be prepared according to the invention are valuable starting materials for dyes, pharmaceuticals and crop protection agents.

EXAMPLE 1

Preparation of 2-amino-4-fluoro-6-methoxypyrimidine (Variant A)

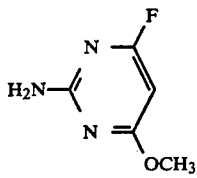

(a) 2-Amino-4,6-difluoropyrimidine 69.7 g (4.1 mol) of liquid ammonia were added at −30° to −20° C. to a stirred mixture of 250 g (1.865 mol) of 2,4,6-trifluoropyrimidine and 3.3 l of diethyl ether within 1 hour. To work up, the reaction mixture was warmed to 25° C. and the precipitate was filtered off. Washing with ether, stirring in water, renewed filtration and drying resulted in 203 g (83% of theory) of the desired product (melting point 214°-216° C.). It was possible by concentrating the ether filtrate to about ⅓ of its volume to isolate a further 20 g (8% of theory) of this compound, of melting point 193°-196° C., from a 1:1 mixture with the isomeric 4-amino compound. Comparative experiment (according to SU-A 547,447—1975)

Under the same reaction conditions as in (a), but with addition and reaction taking place at -10° C., 100 g (0.746 mol) of 2,4,6-trifluoropyrimidine and 29.1 g (1.71 mol) of ammonia yielded 76 g (78% of theory) of the title compound of melting point 212°-213° C., and from the filtrate a further 19.5 g (20% of theory) of a mixture (40:60) of the desired compound and the isomeric 4-amino compound (melting point 195°-196° C.).

(b) 2-Amino-4-fluoro-6-methoxypyrrmidine (Variant A)

27 g of 30% strength sodium methylate (0.15 mol) were added at 65° C. to a stirred suspension of 19.7 g (0.15 mol) of 2-amino-4,6-difluoropyrimidine in 250 ml of absolute methanol within 20 minutes. After the reaction solution had been refluxed for 5 hours it was cooled to 25° C., and the precipitate was removed, washed with a little methanol and then stirred in water. After it had been filtered off, washed with water and dried, 16 9 (74% of theory) of the title compound of melting point 172° C. were obtained A further 3 g (14% of theory) of the title compound of melting point 161°-169° C. were isolated by concentrating the filtrate and washing with methanol and subsequently with water.

EXAMPLE 2

Preparation of 2-amino-6-ethoxy-4-fluoropyrrmidine (Variant A)

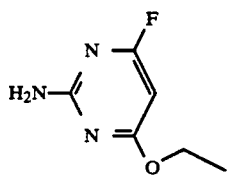

A solution of 25.2 g (0.3 mol) of potassium ethylate in 200 ml of absolute ethanol was added at 78° C. to a stirred suspension of 39.3 g (0.3 mol) of 2-amino-4,6-difluoropyrimidine (see Example 1a) in 150 ml of absolute ethanol within 40 minutes. The mixture was refluxed for 5 hours and then cooled, after which the solvent was removed under reduced pressure. The residue was stirred with water, filtered off, washed with water and dried. 39 g (83% of theory) of the title compound of melting point 121°-123° C. were obtained (cf. Lit. J. Med. Chem. 6 (1963) 688; 61% yield of crude product; melting point after recrystallization: 120.5°-123° C.).

EXAMPLE 3

Preparation of 2-amino-4-fluoro-6-propyloxypyrimidine (Variant A)

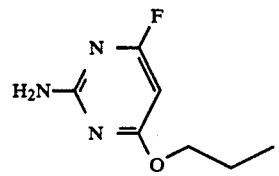

29 4 g (0.3 mol) of potassium propylate were reacted as in Example 1 with 39.3 g (0.3 mol) of 2-amino-4,6-difluoropyrimidine in a total of 400 ml of n-propanol. The solvent was removed from the reaction mixture under reduced pressure, and the residue was washed with petroleum ether. It was subsequently stirred in water, filtered off, washed and dried, resulting in 36.1 g (70% of theory) of the title compound of melting point 63°-66° C.

EXAMPLE 4

Preparation of 2-amino-4-fluoro-6-isopropyloxypyrimidine (Variant A)

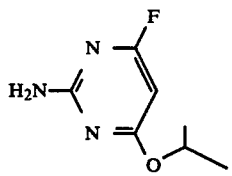

29.4 g (0.3 mol) of potassium isopropylate were reacted as in 1.2 with 39.3 g (0.3 mol) of 2-amino-4,6-difluoropyrimidine (A.1a) in a total of 400 ml of isopropanol. After the working up, washing with petroleum ether and water in the usual manner, 38.5 g (75% of theory) of the title compound of melting point 66°-68° C. were obtained.

EXAMPLE 5

Preparation of 6-allyloxy-2-amino-4-fluoropyrimidine (Variant A)

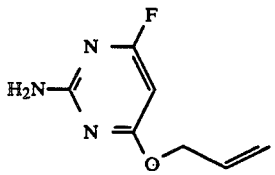

1.14 g (0.0382 mol) of 80% sodium hydride (emulsion in linseed oil) were added at 25° C. under a nitrogen atmosphere to 70 ml of allyl alcohol. To the clear solution obtained after stirring at 40° C. for 20 minutes were added 5.0 g (0.0382 mol) of 2-amino-4,6-difluoropyrimidine, and the mixture was then stirred at 97° C. for 1.5 hours. To work up, the excess alcohol was removed by distillation under reduced pressure, the residue was taken up in methylene chloride, and the solution was washed with water, dried over magnesium sulfate and then freed of solvent. The viscous oil obtained in this way crystallized on trituration with n-pentane. 4.6 g (71.2% of theory) of the title compound of melting point 62°-66° C. were obtained after filtering off, washing with water and drying.

EXAMPLE 6

Preparation of 2-amino-6-cyclohexyloxy-4-fluoropyrimidine (Variant A)

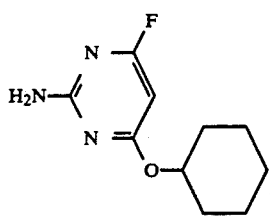

1.14 g (0.0382 mol) of 80% sodium hydride were added at 25° C. under nitrogen to 80 ml of cyclohexanol, after which this mixture was stirred at 120° C. for 2 hours. After it had cooled to 40° C., 5.0 g (0.0382 mol) of 2-amino-4,6-difluoropyrimidine were added, and the mixture was then stirred at 110° C. for 8 hours. After the reaction was complete, the excess cyclohexanol was removed by distillation under reduced pressure, and the residue obtained in this way was dissolved in 30 ml of methanol and induced to crystallize by addition of water. 6.4 g (79.4% of theory) of the title compound of melting point 89°-91° C. were obtained after filtering off, washing with water and drying.

EXAMPLE 7

Preparation of 2-amino-6-benzyloxy-4-fluoropyrimidine (Variant A)

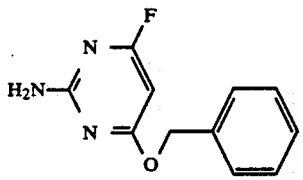

1.14 g (0.0382 mol) of 80% sodium hydride were added at 25° C. under nitrogen to 70 ml of benzyl alcohol, and this mixture was stirred at 100° C. for 30 minutes. After it had been cooled to 40° C., 5.0 g (0.0382 mol) of 2-amino-4,6-difluoropyrimidine were added, and the mixture was then stirred at 100° C. for 5 hours. After the reaction was complete, a little precipitate was filtered off, and the filtrate was concentrated under 1 mbar at a bath temperature of 150° C. The viscous residue obtained in this way was induced to crystallize by trituration with cyclohexane. 6.3 g (75.2% of theory) of the title compound of melting point 96°-98° C. were obtained after filtering off, washing with water and drying.

EXAMPLE 8

Preparation of 2-amino-4-fluoro-6-n-heptyloxypyrimidine (Variant A)

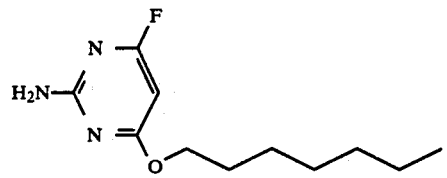

A solution of 1.14 g (0.038 mol) of 80% sodium hydride (suspension in linseed oil) in 30 ml of n-heptanol was added to a stirred mixture of 5 g (0.038 mol) of 2-amino-4,6-difluoropyrimidine in 70 ml of n-heptanol at 20° to 25° C. within 5 minutes. After 2.5 hours working up was carried out as in Example 6. 6.3 g (73% of theory) of the title compound of melting point 30°-32° C. were obtained in this way.

EXAMPLE 9

Preparation of 2-amino-6-(4-chlorophenoxy)-4-fluoropyrimidine (Variant A)

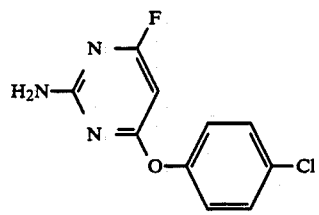

2.52 g (0.038 mol) of 85% sodium hydroxide were dissolved in 50 ml of methanol, 4.9 g (0.0382 mol) of 4-chlorophenol were added, and the mixture was evaporated to dryness. The residue of salt obtained in this way was taken up in 50 ml of N-methyl-2-pyrrolidone and, at 25° C., 5.0 g (0.0382 mol) of 2-amino-4,6-difluoropyrimidine were added, and the mixture was stirred at 140° C. for 4 hours. After the reaction mixture had been cooled to 25° C. it was stirred into 500 ml of water, and the resulting precipitate was isolated. 7.4 g (81% of theory) of the title compound of melting point 223°-226° C. were obtained in this way.

EXAMPLE 10

Preparation of 4,6-difluoro-2-n-propylaminopyrimidine (Variant A)

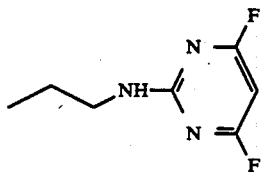

13.0 g (0.22 mol) of n-propylamine were added at −20° C. to a mixture of 13.4 g (0.1 mol) of 2,4,6-trifluoropyrimidine in 150 ml of diethyl ether within 20 minutes. After stirring at −20° C. for 1 hour and at 25° C. for 1 hour, the precipitate was filtered off, and the organic phase was washed with water, dried and concentrated under reduced pressure. 15.8 g (91.3% of theory) of the title compound were obtained as an oil ($n_D^{23}=1.4965$).

EXAMPLE 11

Preparation of 2-allylamino-4,6-difluoropyrimidine
(Variant A)

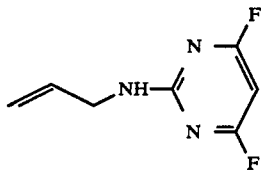

11.1 g (65% of theory) of the title compound of melting point 52°-54° C. were obtained as in Example 10 from 12.5 g (0.22 mol) of allylamine and 13.4 g (0.1 mol) of 2,4,6-trifluoropyrimidine in 150 ml of ether.

EXAMPLE 12

Preparation of 2-benzylamino-4,6-difluoropyrimidine
(Variant A)

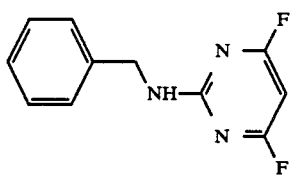

23.5 g (0.22 mol) of benzylamine were added at −20° C. to a stirred mixture of 13.4 9 (0.1 mol) of 2,4,6-trifluoropyrimidine in 150 ml of diethyl ether within 15 min, and the mixture was stirred at this temperature for 1 hour. After a further hour at 25° C., working up was carried out as in Example 10. 21.4 g (98% of theory) of the title compound of melting point 70°-73° C. were obtained in this way.

EXAMPLE 13

Preparation of 2-amino-6-fluoro-4-methoxyypyrimidine
(Variant B)

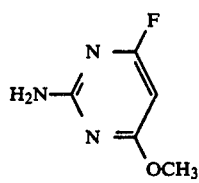

(a) 2,4-Difluoro-6-methoxypyrimidine 335.8 g (1.865 mol) of 30% strength sodium methylate (in methanol) were added at −20° C. to a mixture of 250 g (1.865 mol) of 2,4,6-trifluoropyrimidine in 1.4 l of methanol within 45 minutes, and the mixture was stirred at this temperature for a further 30 minutes. The reaction mixture was then allowed to warm to 25° C. and concentrated to about 1/5 of its volume.

The mixture obtained in this way was partitioned between diethyl ether and water, after which the organic phase was dried over magnesium sulfate and concentrated. Distillation (1.1 m column, 3 mm V-shaped packing) resulted in 141.6 g (52% of theory) of the title compound of boiling point 144°-145° C.

Distillation without a column of the distillation residue resulted in 114.4 g (42% of theory) of 4,6-difluoro-2-methoxypyrimidine of boiling point: 157°-161° C.

(b) 2-Amino-6-fluoro-4-methoxypyrimidine 13.6 g (0.8 mol) of ammonia in 30 ml of methyl tert.-butyl ether were added at −20° to −10° C. to a stirred mixture of 52 g (0.356 mol) of 2,4-difluoro-6-methoxypyrimidine in 300 ml of methyl tert.-butyl ether within 20 minutes. After a further 2 hours at −15° C. and 3 hours at 25° C., the precipitate was filtered off with suction, washed with methyl tert.-butyl ether, stirred with water, filtered off, washed again and subsequently dried, resulting in 36.1 g (71% of theory) of the title compound of melting point 171°-173° C.

EXAMPLE 14

Preparation of 4-fluoro-6-methoxy-2-methylaminopyrimidine
(Variant B)

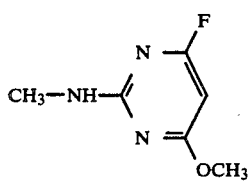

46.8 g of a 40% strength solution of methylamine in water (0.605 mol) were added at 0° to 2° C. to a stirred mixture of 41.9 g (0.287 mol) of 2,4-difluoro-6-methoxypyrimidine (Example 13a) and a spatula-tip of triethylbenzylammonium chloride (phase-transfer catalyst) in 100 ml of methyl tert.-butyl ether within 30 minutes. After 1 hour at 0° C. and 3 hours at 25° C., the organic phase was separated off, washed with water and concentrated under reduced pressure. The residue was stirred with pentane, resulting in 39.9 g (88% of theory) of 4-fluoro-6-methoxy-2-methylaminopyrimidine of melting point 78°-80° C.

EXAMPLE 15

Preparation of 2,4-difluoro-6-methoxypyrimidine
(Variant B)

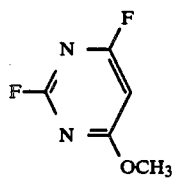

250 g (1.865 mol) of 2,4,6-trifluoropyrimidine in 2.5 l of methanol were boiled under a nitrogen atmosphere for 4 hours and subsequently distilled (formation of dimethyl ether and decomposition with longer reaction times).

Fraction I (no column): 70.0 g (28% of theory) of unreacted 2,4,6-trifluoropyrimidine of boiling point 104°-110° C.

Fraction II (packed column as in Example 13a) 111.6 g (41% of theory) of the title compound of boiling point 144°-145° C.

Fraction III (packed column as in Example 13a) 24.5 g (9% of theory) of 4,6-difluoro-2-methoxypyrimidine of boiling point 157°–161° C.

The yield based on the conversion of 72% of 2,4,6-trifluoropyrimidine is 57% of theory of the title compound, and 12.5% of theory of the 2-methoxy compound.

EXAMPLE 16

Preparation of 2,4-difluoro-6-methoxypyrimidine (Variant B)

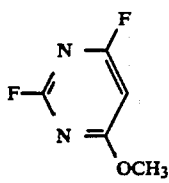

3.8 g (0.0373 mol) of triethylamine were added at −20° C. to a mixture of 5 g (0.0373 mol) of 2,4,6-trifluoropyrimidine in 50 ml of methanol within 5 minutes, and the mixture was stirred at this temperature for a further 40 minutes. After the reaction was complete, the mixture was warmed to 25° C. and the excess methanol was removed by distillation under reduced pressure. The residue obtained in this way was partitioned between methylene chloride and water, and the organic phase was dried over magnesium sulfate and concentrated. 4.6 g (85% of theory) of an isomer mixture which, according to investigation by gas chromatography, contained 46% of the title compound and 48% of 4,6-difluoro-2-methoxypyrimidine were obtained in this way.

EXAMPLE 17

As Example 16, but with 4 g (0.0373 mol) of 2,6-lutidine in place of triethylamine. 4.8 g (88.9% of theory) of the isomer mixture which, according to the gas chromatogram, contained 61.5% of the title compound to 38.5% of the 2-methoxy isomer were obtained in this way.

EXAMPLE 18

Preparation of 2-cyclohexylamino-4-fluoro-6-methoxypyrimidine (Variant B)

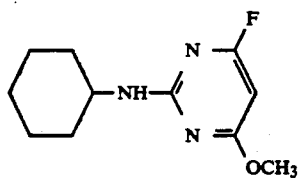

10.1 g (0.102 mol) of cyclohexylamine were added at 0°-to 2° C. to a mixture of 7.3 g (0.05 mol) of 2,4-difluoro-6-methoxypyrimidine in 50 ml of methyl t.-butyl ether within 15 minutes. After 1 hour at 0° C. and 3 hours at 25° C., the resulting precipitate was filtered off, and the filtrate was washed with water, dried over magnesium sulfate and concentrated. 8.3 g (73.8% of theory) of the title compound were isolated as an oil ($n_D^{23}$=1.5211) after chromatography of the residue obtained in this way.

EXAMPLE 19

Preparation of 4-fluoro-2-n-hexylamino-6-methoxypyrimidine (Variant B)

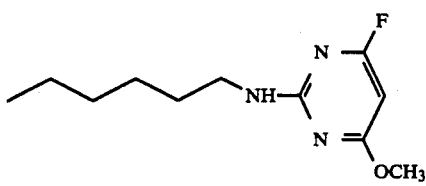

15.6 g (0.154 mol) of n-hexylamine were added at 0° to 2° C. to a stirred mixture of 10.4 g (0.071 mol) of 2,4-difluoro-6-methoxypyrimidine in 60 ml of methyl t.-butyl ether within 15 minutes. After 1 hour at 0° C., 4 hours at 25° C. and working up as in B 2-3, 9.6 g (60% of theory) of the title compound of $n_D^{23}$=1.4938 were obtained.

I claim:

1. A process for the preparation of a 2-amino-4-fluoropyrimidine derivative of the general formula I

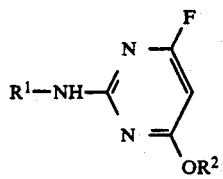

where $R^1$ is hydrogen, alkyl, alkenyl, alkynyl, cycloalkyl, phenyl or benzyl, it being possible for the aromatic rings to be substituted once to three times by radicals inert to the reaction conditions, $R^2$ is one of the $R^1$ radicals with the exception of hydrogen, by reaction of 2,4,6-trifluoropyrimidine (II)

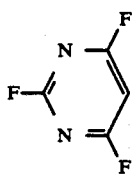

in an aprotic polar organic solvent with an amine of the formula III $R^1$—NH$_2$     III to give the 2-aminodifluoropyrimidine derivative of the formula IVa mixed with IVb

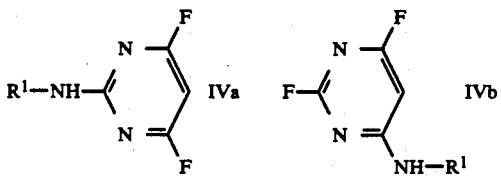

separation of IVa out of the resulting reaction mixture and subsequent reaction of IVa with an alcohol of the formula V $R^2$—OH     V in the presence of a base at from 0° to 180° C. to give the 2-amino-4-fluoropyrimidine derivative I, which comprises carrying out the reaction of 2,4,6-trifluoropyrimidine II with the amine III at from −80° C. to −15° C., and reacting the 2-aminodifluoropyrimidine derivative IVa with the alcohol V in the presence of an organic base to give the 2-amino-4-fluoropyrimidine derivative I.

2. A process for the preparation of a 2-amino-4-fluoropyrimidine derivative of the general formula I as claimed in claim 1, by reaction of 2,4,6-trifluoropyrimidine (II) in an inert organic solvent in the presence of a base with an alcohol of the formula V as claimed in claim 1 to give the 2,4-difluoropyrimidine ether VIa mixed with the 4,6-difluoropyrimidine ether VIb

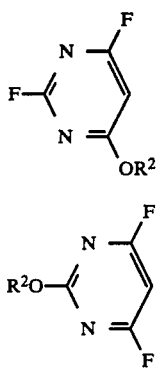

separation of VIa out of the resulting reaction mixture and subsequent reaction of VIa in an aprotic polar solvent with an amine of the formula III as claimed in claim 1 to give the 2-amino-4-fluoropyrimidine derivative I, which comprises reacting the alcohol III or its alkali metal or alkaline earth metal salt in the alcohol as the solvent or in a cation-complexing solvent at from −40° C. to 120° C. and carrying out the subsequent reaction of VIa with the amine III at from −40° C. to 100° C.

3. A process as claimed in claim 1, wherein the solvent used in the reaction of II with III is an ether, ester or halogenated hydrocarbon with a solvent polarity $E_T^N$ below 0.35.

4. A process as claimed in claim 1, wherein the amine III is employed in 1.8 to 2.2 mol-equivalents relative to II.

5. A process as claimed in claim 1, wherein a tertiary amine is used as organic base in the reaction of the 2-aminodifluoropyrimidine IVa with the alcohol V.

6. A process as claimed in claim 5, wherein the tertiary amine is added in 0.9 to 1.2 mol-equivalents relative to IVa.

7. A process as claimed in claim 1, wherein an alkali metal or alkaline earth metal salt of the alcohol V is used as organic base in the reaction of the 2-aminodifluoropyrimidine IVa with the corresponding alcohol.

8. A process as claimed in claim 7, wherein the alkali metal or alkaline earth metal alcoholate is employed in 0.9 to 1.2 mol-equivalents relative to IVa.

9. A process as claimed in claim 7, wherein the 2-aminodifluoropyrimidine IVa is reacted with an alkali metal or alkaline earth metal salt of the alcohol V in the presence of a solvent which complexes the metal cation and has a solvent polarity $E_T^N$ of 0.5 to 0.3.

10. A process as claimed in claim 9, wherein the alkali metal or alkaline earth metal salt of the alcohol V is employed in 0.9 to 1.2 mol-equivalents relative to IVa.

11. A process as claimed in claim 10, wherein the solvent is added in 5 to 15 mol-equivalents relative to IVa.

12. A process as claimed in claim 1, wherein the amine III is added to a solution of 2,4,6-trifluoropyrimidine (II).

* * * * *